Figure 2:
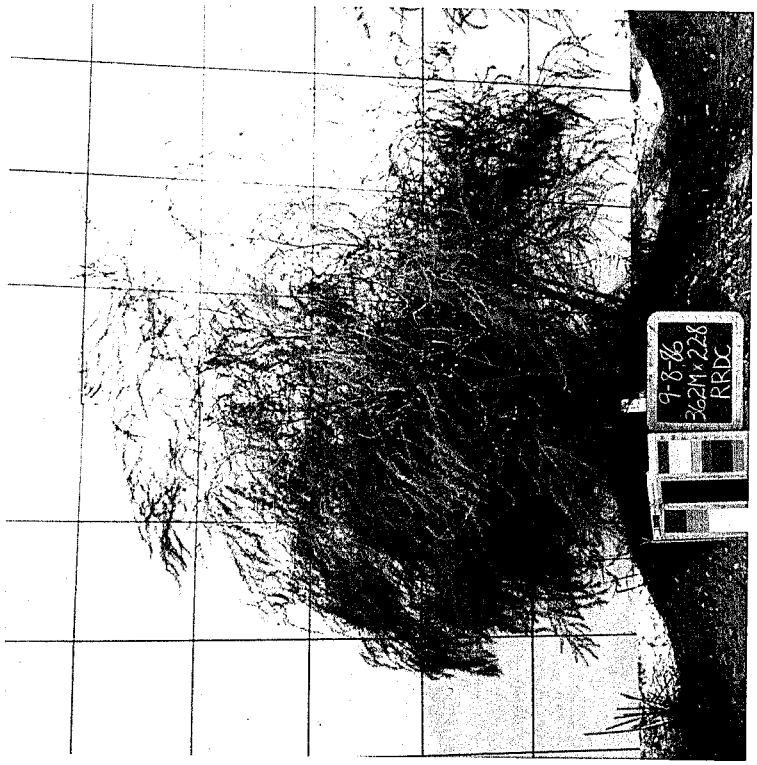

United States Patent [19]

Ellison et al.

[11] Patent Number: Plant 6,965

[45] Date of Patent: Aug. 1, 1989

[54] ASPARAGUS PLANT — 'JERSEY GENERAL'

[75] Inventors: J. Howard Ellison, Milltown; John J. Kinelski, Princeton, both of N.J.

[73] Assignee: Rutgers University, New Brunswick, N.J.

[21] Appl. No.: 159,680

[22] Filed: Feb. 24, 1988

[51] Int. Cl.[4] ..... A01H 5/00

[52] U.S. Cl. ..... Plt./89

[58] Field of Search ..... Plt./89

*Primary Examiner*—James R. Feyrer

*Attorney, Agent, or Firm*—Frank B. Robb

[57] ABSTRACT

There is disclosed a high volume producing Asparagus plant having a very good tolerance to Fusarium infestation, where other commercial asparagus cannot be grown profitably, very high production of marketable spears and excellent volume of jumbo spears with quality maintained even in hot weather, the plant being vigorous, high headed and well adapted to light sandy soil.

1 Drawing Sheet

BACKGROUND OF THE INVENTION

This invention relates to a new Asparagus plant which we have developed during a long continuing program having many different objectives, some of these relating to the production of plants which are resistant to diseases, have high quality spears, grow in various kinds of soil and produce greater quantities of jumbo spears.

The instant hybrid which is described in detail herein, we have chosen to designate as "Jersey General" for commercial identification since it is a male plant and is an example of our program with some particularly outstanding attributes.

The plant herein referred to, denominated as above noted, is a vigorous, high headed plant especially well adapted to light sandy soil found in southern New Jersey, where it has been grown, establishing its ability to produce greater quantities of jumbo spears than the variety "Greenwich", which is the subject of U.S. Plant Pat. No. 5,550.

DESCRIPTION OF THE INVENTION

In addition, when compared with another variety which we have developed and known as "Jersey Giant", the subject of U.S. Plant Pat. No. 5,551, our new plant provided a sixty-five percent greater yield as recorded over a two year period, data for the comparison being set forth hereinafter, data for other asparagus plants developed by us also being included.

Under other conditions as when the soil is a heavier sandy loam than the sandy soil referred to, which was Fusarium infested, near New Brunswick, N.J., our new plant produced thirty-five percent more jumbo spears than the next highest producing cultivar, and a total yield one hundred sixty-nine percent more jumbo spears than the average of a large number of other hybrids. The total marketable yield of our new hybrid was seventy percent greater than the average of sixteen other hybrids.

Tight spear tips which do not open readily in hot weather are another distinguishing aspect of our new plant, where other cultivars are prone to do so, resulting in lower spear quality.

We have found it very helpful to assemble data of many different kinds in view of our continuing development program, such data enabling us to not only distinguish but to direct our efforts to effecting the production of most improved plants.

We have caused our new plant to be asexually reproduced by crown division and found it to come true in successive generations.

Figure 1:
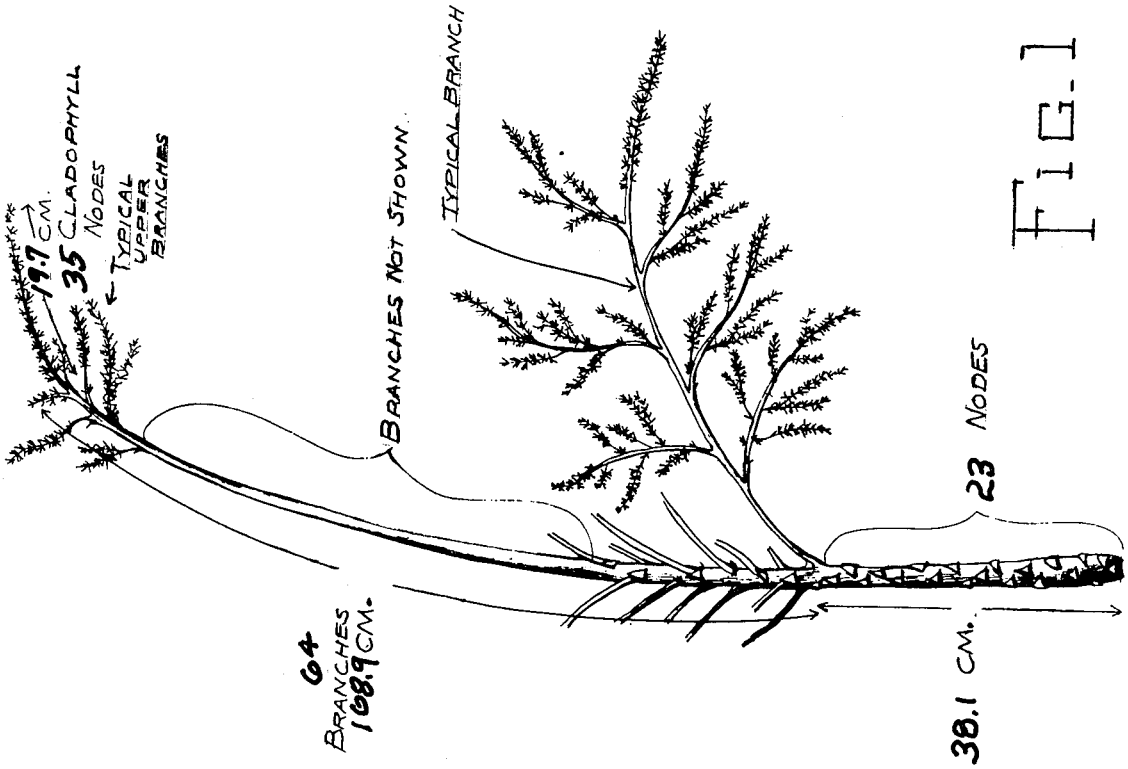

In the accompanying drawing,

FIG. 1 discloses some of our data as applied to a typical plant,

And in FIG. 2, a color disclosure is provided, wherein the colors are described in reference to the Munsell Color Limit Cascade of Kollmorgen Corp., Baltimore, Md., and as nearly true as a photograph of this kind can provide.

As will be understood only representative data is supplied so that comparison with other plants described by us, may be made and assist in identifying our plants as well as distinguish from existing plants previously developed both by us and others.

BOTANICAL DESCRIPTION

STALK DATA

The number "1", in parenthesis below, indicates the measurements presented were taken from the largest stalk. All measurements below are in centimeters unless otherwise indicated.

| | |
|---|---|
| Number of nodes below first branch(1) | 23 |
| Number of cm. from crown to first branch(1) | 38.1 |
| Number of branches(1) | 64 |
| Number cm. between first and last branch(1) | 168.9 |
| Internode length in cm. between branches(1) | 2.64 |
| Number of cladophyll nodes beyond last branch(1) | 35 |
| Number of cm. beyond last branch(1) | 19.7 |
| Internode length in cm. beyond last branch(1) | 0.56 |
| Largest stalk diameter in mm | 21.5 |
| Mean diameter of three largest stalks in mm | 19.5 |
| Number of stalks | 19 |
| Stalk vigor index(Number × Mean Diam.) | 7,225 |
| Mature stalk color, bloom removed. Color No. (1) | 22–12 |
| Highest headed stalk cm. to first branch | 57.2 |
| Length of highest headed stalk | 228.6 |
| FLOWER DATA | |
| Petal tip (yellow) Color No. (1) | 26–3 |
| Petal base (purple) Color No. (1) | 46–7 |
| Flower length mm | 6.8 |
| Flower width at midpoint mm | 2.7 |

THE SPECIFICATIONS TO FOLLOW ARE PRESENTED IN CENTIMETERS UNLESS OTHERWISE STATED.

CLADOPHYLL DATA

-continued

| BOTANICAL DESCRIPTION | |
|---|---|
| Number per node | 4.87 |
| Length (mm) | 12.00 |
| Width (mm) | 0.129 |

ASPARAGUS HYBRID YIELD

| | JUMBO Mean lb/A | 2 TOTAL MARKET-ABLE lb/A |
|---|---|---|
| JERSEY GENERAL 362 M × 22-8 | 758 | 1537 |
| GREENWICH 53 × 22-8 | 428 | 1084 |
| JERSEY GIANT 56 × 22-8 | 336 | 1050 |

-continued

| BOTANICAL DESCRIPTION | | |
|---|---|---|
| JERSEY CENTENNIAL JC(RM-202) | 460 | 946 |

1 Larger than 10/16" diameter, 9" spears
2 Diameter 6/16' and larger, 9" spears

We claim:

1. A new and distinct variety of Asparagus plant as hereinbefore shown and described, characterized particularly as to novelty by the unique combination of particular adaptation to light sandy soil, substantially overall greater yield than other prior varieties, excellent production of jumbo spears, high marketable total yield, spear tips which remain tight even in hot weather, and good production in Fusarium infested heavy sandy loam.

* * * * *